(12) United States Patent
Schumacher et al.

(10) Patent No.: US 7,368,282 B2
(45) Date of Patent: May 6, 2008

(54) PROCESS AND DEVICE FOR DETERMINING THE ACTIVITY OF ENZYMES IN LIQUIDS, OR THE CONCENTRATION AND/OR ACTIVITY OF INHIBITORS IN LIQUIDS

(76) Inventors: Johannas Schumacher, Hildastrasse 9, D69181 Leimen (DE); Bernd Werle, Konrad-Adenauer-Ring 6, D69214 Eppelheim (DE)

( * ) Notice: Subject to any disclaimer, the term of this patent is extended or adjusted under 35 U.S.C. 154(b) by 171 days.

(21) Appl. No.: 10/326,626

(22) Filed: Dec. 19, 2002

(65) Prior Publication Data
US 2003/0087426 A1 May 8, 2003

Related U.S. Application Data

(63) Continuation of application No. 09/753,753, filed on Jan. 3, 2001, now abandoned, which is a continuation of application No. 09/316,539, filed on May 21, 1999, now Pat. No. 6,171,851, which is a continuation of application No. 08/793,833, filed as application No. PCT/DE96/01087 on Jun. 19, 1996, now Pat. No. 5,935,846.

(30) Foreign Application Priority Data

| Jun. 20, 1995 | (DE) | 195 22 255 |
| Jul. 29, 1995 | (DE) | 195 27 880 |
| May 3, 1996 | (DE) | 196 17 731 |

(51) Int. Cl.
*C12M 1/40* (2006.01)
(52) U.S. Cl. .............. 435/288.6; 435/288.7; 435/286.5; 435/287.9
(58) Field of Classification Search .............. 435/288.6
See application file for complete search history.

(56) References Cited
U.S. PATENT DOCUMENTS
3,983,001 A 9/1976 Čoupek et al.
4,030,977 A * 6/1977 Fujii et al. ................... 435/219
4,243,753 A * 1/1981 Regnier et al. .......... 435/288.6

(Continued)

FOREIGN PATENT DOCUMENTS
DE 2323422 11/1973

(Continued)

OTHER PUBLICATIONS

Afting et al., "Two-Step Affinity-Chromatographic Purification of Cathespsin D from Pig Myometrium with High Yield", *Biochem. J.*, 1981, vol. 197, pp. 519-522.

(Continued)

*Primary Examiner*—William H. Beisner
(74) *Attorney, Agent, or Firm*—Fitch, Even, Tabin & Flannery

(57) ABSTRACT

A process and device are disclosed to determine the activity of enzymes in liquids in a largely automatic manner. The device for carrying out this process has a column (1) with a chromatographic carrier for treating a measurement sample. The carrier is mixed with a substance capable of binding to an enzyme inhibitor present in the measurement sample and that corresponds to at least one enzyme. A measurement sample supply (2) is associated to one end of the column (1). A valve/pump arrangement (7, 11, 14, 15) for filling at least one test tube (5) with a carrier and at least part of the measurement sample is connected downstream of the column (1), in the flow direction of the measurement sample. The carrier is dissociated into cleavage products by the action of the enzyme. The rise in concentration per unit of time of at least one of the cleavage products of the carrier is sensed during an incubation time. As an alternative or supplementary step, the enzyme that corresponds to at least one enzyme inhibitor is extracted by chromatography from a measurement sample to detect enzyme inhibitors in liquids and the thus treated measurement sample is tested for inhibitor concentration and/or activity.

19 Claims, 5 Drawing Sheets

U.S. PATENT DOCUMENTS

| | | | | |
|---|---|---|---|---|
| 4,699,718 A | * | 10/1987 | Jones et al. | 210/659 |
| 4,762,617 A | * | 8/1988 | Stevens | 210/635 |
| 5,416,023 A | * | 5/1995 | Binder et al. | 435/287.9 |
| 5,935,846 A | * | 8/1999 | Schumacher et al. | 435/288.6 |
| 6,171,851 B1 | * | 1/2001 | Schumacher et al. | 435/288.6 |

FOREIGN PATENT DOCUMENTS

| | | |
|---|---|---|
| DE | 3613407 | 10/1987 |
| EP | 0019638 | 12/1970 |
| EP | 0329190 | 8/1989 |
| EP | 0335354 | 10/1989 |
| GB | 2213262 | 8/1989 |

OTHER PUBLICATIONS

Anastasi et al., "Cystatin, A Protein Inhibitor of Cysteine Proteinases", *Biochem. J.*, 1983, vol. 211, pp. 129-138.

Koohmaraie et al., "Comparisons of Four Methods for Quanitifaction of Lysosomal Cysteine Proteinase Activities" *J. Anim. Sci.*, 1990, Vo. 68, pp. 2362-2370.

Brinkman et al., "Post- Column Reactors for Sensitive and Selective Detection in High-Performance Liquid Chromatography Categorization and Applications", *Journal of Chromotography*, 492 (1989) 251-298.

De Jong et al. "Chemiluminscence Detection for High Performance Liquid Chromatography of Biomedical Samples", *Journal of Chromotography*, 492 (1989) 319-343.

Schroeder et al. "Enzyme-Selective Detector Systems for High-Pressure Liquid Chromatography", *Journal of Chromotography*, 134 (1977) 83-90.

* cited by examiner

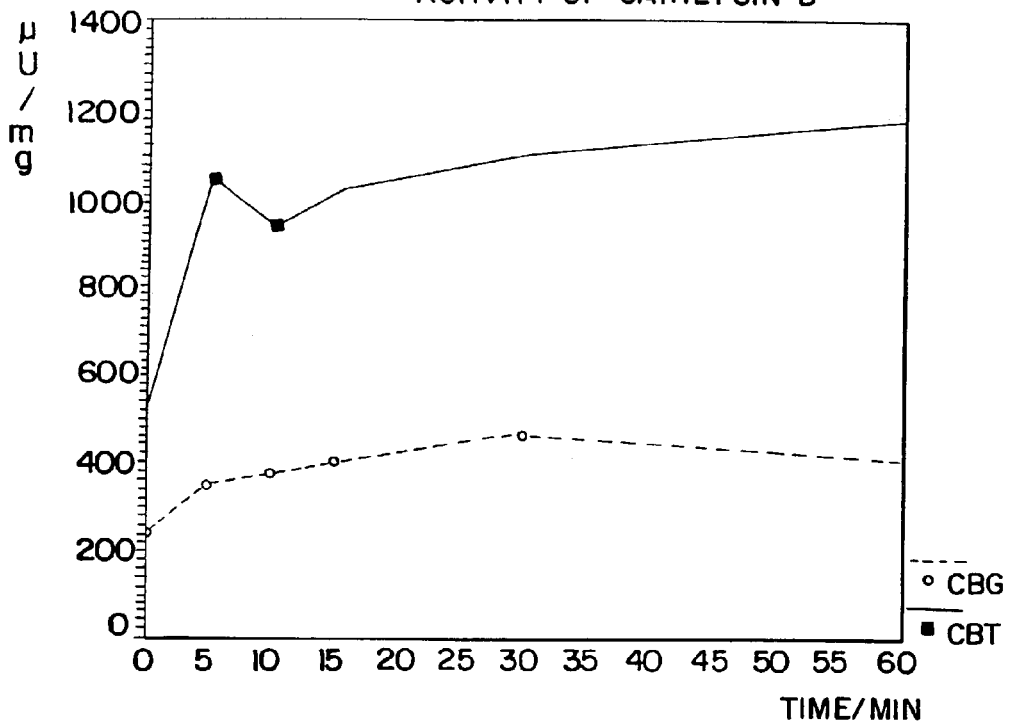
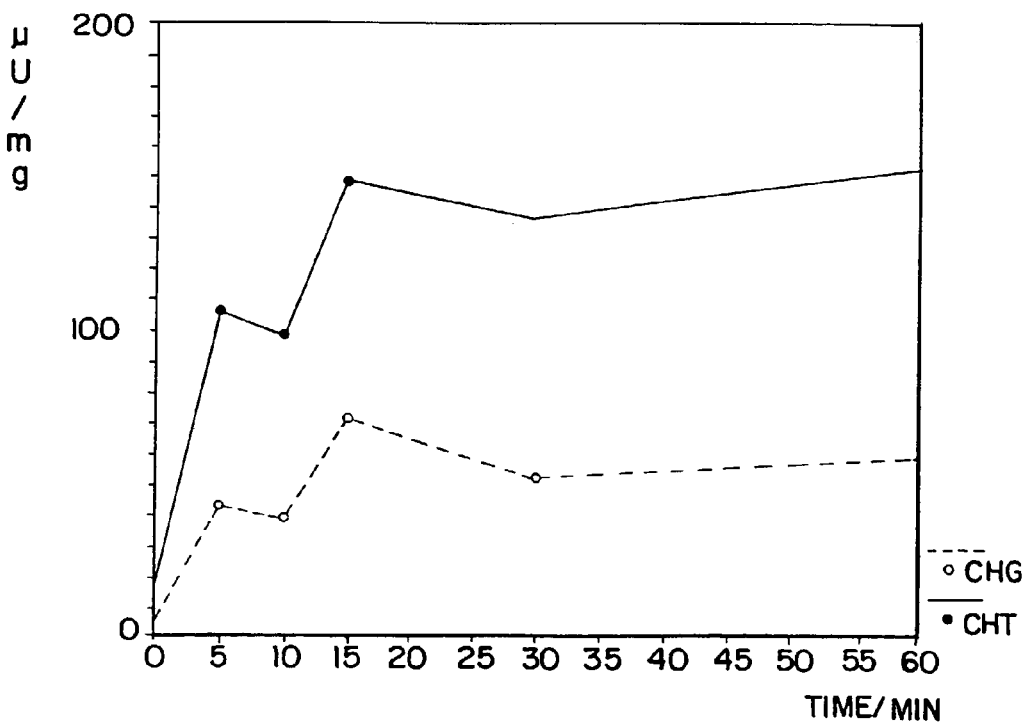

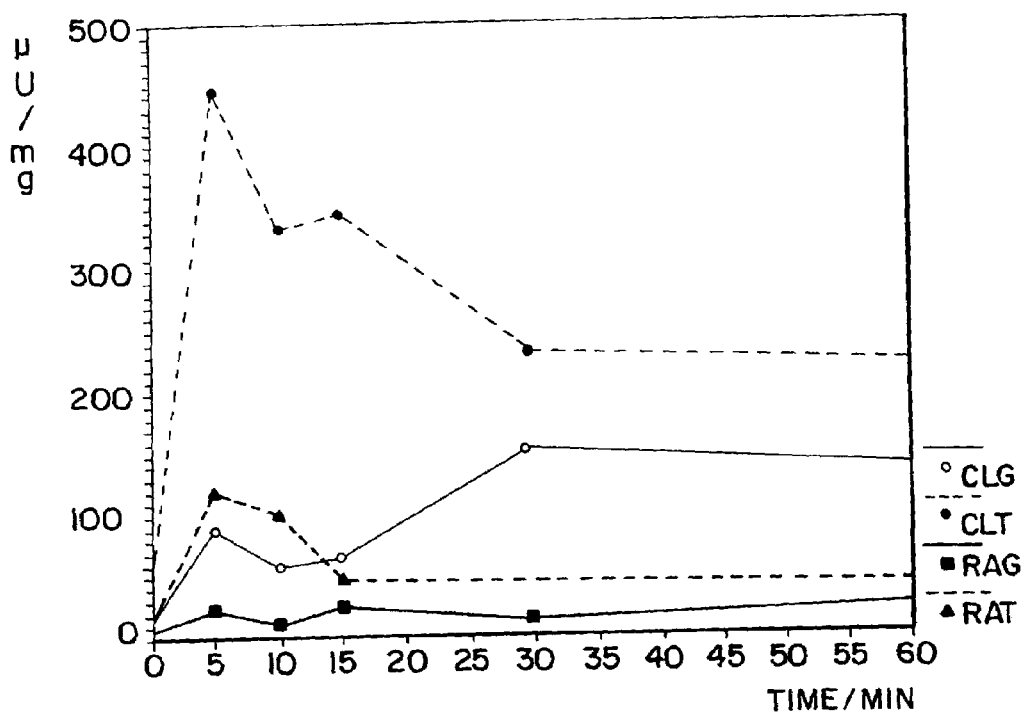
FIG. 6 ACTIVITY OF CATHEPSIN L
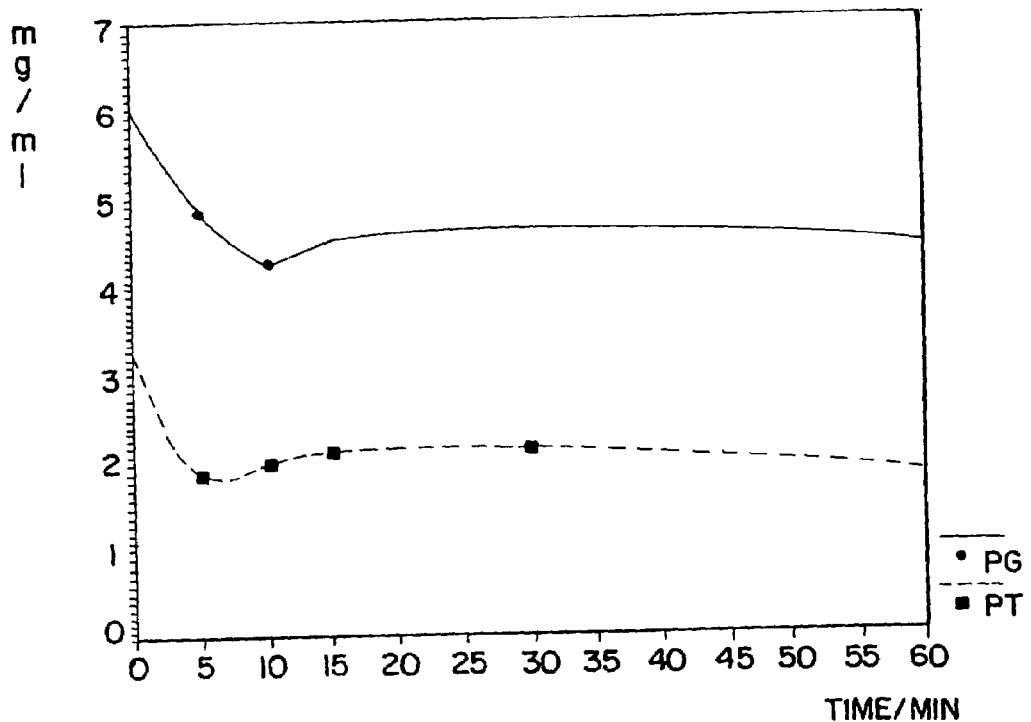
FIG. 7 AMOUNT OF PROTEIN

PROCESS AND DEVICE FOR DETERMINING THE ACTIVITY OF ENZYMES IN LIQUIDS, OR THE CONCENTRATION AND/OR ACTIVITY OF INHIBITORS IN LIQUIDS

This application is a continuation of prior application Ser. No. 09/753,753, filed Jan. 3, 2001, now abandoned, which is a continuation of prior application Ser. No. 09/316,539, filed May 21, 1999, now U.S. Pat. No. 6,171,851, which is a continuation of prior application Ser. No. 08/793,833, filed Feb. 18, 1997 as the national phase application of application No. PCT/DE96/01087, filed on Jun. 19, 1996, now U.S. Pat. No. 5,935,846, which claims the benefit of DE 19522255, filed Jun. 20, 1995, DE 19527880, filed Jul. 29, 1995 and DE 19617731, filed May 3, 1996.

The invention discloses a process and a device for determining the activity of enzymes in liquids, or the concentration and/or activity of inhibitors in liquids.

The determination of enzyme activities in extracts of plants, suspensions of bacteria, homogenates and body fluids such as blood serum, blood plasma, urine, punctate, liquor, cell lines or homogenated tissue has obtained an essential importance for diagnosis, follow up and therapy control.

For example, the discrimination between enzyme proteins and the other proteins in blood serum by chemical means is exceedingly questionable, because the concentrations of the individual enzymes in body fluids are extremely small. The concentration of glutamate-oxaloacetate transaminase in blood serum of a healthy individual is 0,1 µg/ml, for example. As for comparison, the total protein concentration in blood serum is in the range between 60 to 80 mg/ml, that is, the ratio of these two concentrations is about 1:700.000. Since the determination of the enzyme concentration by chemical means is questionable, the activity of the enzyme is calculated from the rate of its reaction with a suitable substrate.

The so called ELISA assay is known from clinical chemistry. This immunoassay measures the concentration of an enzyme and its corresponding enzym-inhibitor complex present in a tissue or any other sample. Measuring the enzyme activity by this method is impossible, as it measures concentrations regardless to the actual status of the enzyme, active or inhibited.

According to known techniques the activity of an enzyme is measured in such cases by removing at first the enzyme inhibitors corresponding to the enzyme and afterwards determining the activity of the enzyme. The known processes are very laborious, referring to the samples to be measured being tissues as well as to the method, how to remove the enzyme inhibitors from the sample. This method comprises adding to the sample a substance capable of binding the enzyme inhibitors, incubating the so manipulated sample during a definite time to complete the binding of the enzyme inhibitors along with as much homogenous mixing as possible of the sample with the said substance and finally, separating the so manipulated sample from the said substance.

Starting from this point, the purpose of the present invention is to disclose a process and a device for measuring the activity of enzymes in fluids by running the method of measurement largely or completely automatically and also effectively, and for determining the concentration and/or activity of inhibitors in fluids additionally or alternatively.

The inventive process manages the above mentioned problem according to the features of the claims. Accordingly, a process is arranged for measuring enzyme activities in fluids, which comprises withdrawing enzyme inhibitors, that correspond to at least one of the enzymes in the sample, or enzymes, that correspond at least to one inhibitor, adding a substrate to the sample manipulated in this manner, so as to get cleavage products from the substrate by reacting with the enzyme, and detecting the increasing concentration per unit of time of at least one of these cleavage products during an incubation time. The said process is characterized by withdrawing the enzyme inhibitors or enzymes from the sample by means of chromatography.

According to the said invention, it was discovered, that it is possible to remove the enzyme inhibitors from the sample without as much homogenous mixing as possible of the corresponding substance and the sample, and without a following laborious separation process. In connection with this, it was discovered, that one can perform mixing and separation virtually in one step. The said invention has the special advantage, that it enables one now to measure enzyme activities in fluid samples, that is, all kinds of body fluids as well as homogenated tissues, whereby the withdrawing of the enzyme inhibitors by means of chromatography makes it possible, to run the process largely automatically.

For that purpose, the sample is passed in a useful manner through a column filled with a chromatographic carrier, that is treated with a substance capable of binding the enzyme inhibitors. As a result, the enzyme inhibitor is getting concentrated on the column, so as to achieve at the same time an isolation method for these enzyme inhibitors, in a sort of way a side effect of the inventive process.

In order to correlate the results of different measurements, it is necessary to keep to definite experimental conditions. This can be done by diluting the manipulated sample, that is the sample released from the enzyme inhibitors, with a suitable column buffer in a definite manner. Moreover, one may admix a suitable measuring buffer to the sample depending on experimental conditions and the enzyme activities to be measured. In a convenient variant of the inventive process, the assay, that is, the mostly diluted sample together with the test substrate, which reacts with the enzyme to be measured to yield cleavage products, is thermostated during the incubation time.

On principle, there are various possibilities, to detect the concentration increase per unit of time of at least one of the cleavage products of the substrate during the incubation time. It is especially useful, to detect the increase of the concentration by means of fluorescence measurements, as in-this way one can observe the concentration increase during the reaction time particulary well.

Moreover, the purpose of the present invention is accomplished by a device in order to measure the activity of enzymes in fluids according to the feature of claim 7. Accordingly, there is provided a column filled with a chromatographic carrier, which is treated with a substance capable of binding enzyme inhibitors corresponding to at least one of the enzymes present in the sample. A sample supply tube is connected in series to one end of the column. To the other end of the column a valve/pump arrangement is connected in series, by which one can fill a substrate as well as at least a portion of the sample into the test tube. Finally, there is provided a detector for measuring the concentration increase per unit of time of at least one of the cleavage products of the substrate.

According to the said invention, it was discovered, that one can run the process of determining enzyme activities and activities and/or concentrations of inhibitors in fluids, in an arrangement consisting of devices connected in series. This process is also characterized in that by means of chromatography enzyme inhibitors corresponding to an enzyme are withdrawn from the sample. In order to do this, the sample is directed successively through the different stations of the arrangement, so that one needs not withdraw the sample at any of these stations in order to manipulate it especially. In particular it is convenient, that the measurements are carried out automatically, as the individual components of the arrangement are steered and controlled automatically.

An effective arrangement of the inventive device allows one to use the column repeatedly; that is, one can measure several samples serially. For that purpose the column contains an excess of the substance capable of binding the enzyme inhibitors in the various samples. Definitely, the capacity of the column is only limited by the amount of excess of this substance.

Moreover, it is convenient, that the column is exchangeable. In this case an used up column can be replaced by a new one. On the other hand, one can prepare the inventive device for different measurements, that is, for measuring activities of different enzymes. For in that case one has to remove different enzyme inhibitors from different samples. Therefore, one has to prepare the column with different substances.

It is convenient with regard to the measuring process running automatically, when the sample supply tube can be fed alternatively from a sample supply, such as a rondel, or from a reservoir containing column buffer. The column buffer is passed through the column, in order to avoid, that the preceding sample mingle with the following different sample giving inaccurate values. As long as the process is running automatically, the sample supply tube will be fed alternatively from the sample supply or from the reservoir, which is filled with column buffer. In this case it is also convenient, that there is a controll device provided, which is connected in series to the column in order to check the purity of the column buffer discharged from the column. Such a control device may work, for example, by means of photometry or may include means for measuring the electrical conductance of fluids discharged from the column.

As already mentioned, the column buffer, which is applied just after a sample has passed through the column, serves as a wash liquid for the column and dilutes the sample. In order to evaluate the recorded values und to establish definite experimental conditions, in a convenient arrangement of the inventive device, a measuring device is connected in series to the column to determine the degree of dilution of the sample with the column buffer. Such a device may include, for example, means of measuring the volume of liquids. Usually, the volume of the sample is known, therefore, it is sufficient, to determine the volume of the added column buffer or the total volume of the sample plus the added column buffer.

According to the kind of sample and the applied column buffer, it may be convenient also to provide a device in order to get a homogenous mixture of the manipulated sample and the column buffer.

Often it is necessary, to mix to the sample, and if need be, to the column buffer and to the substrate in the test tube a measuring buffer by means of the valve/pump arrangement in order to establish definite experimental conditions. In this connection means turned out to be convenient for thermostating the test tube.

As already suggested in connection with the inventive process, it is convenient, that the detector for detecting the concentration increase of one of the cleavage products of the substrate includes a fluorescence spectrometer.

For diagnosing it is often necessary to compare measurements of enzyme activities from untreated with such form treated blood serum. For that purpose, it is convenient, that there is provided at least one switching valve between the sample supply tube and the column of this inventive device, which enables one, to discharge the sample in the test tube alternatively by passing through the column or by bypassing the column. In this way, untreated samples can be measured, as well as such samples, from which the enzyme inhibitors are removed.

In a convenient improved embodiment of the inventive device, it is provided at least one additional valve in order to feed the column and the valve/pump arrangement with a buffer, that serves as wash liquid. In such a convenient way, it is possible to wash the whole apparatus.

Finally, it may be mentioned, that the inventive device can be run automatically by means of a computer, which controlles the sample-feeding, and if need be, the feeding with column buffer, and coordinates the determination of the dilution of the sample, and if need be, the mixing and charging of the test tubes. Moreover, the computer may serve to record and evaluate the concentration increase per unit of time of one of the cleavage products.

There are different ways to arrange and improve the conclusions of the present invention in a convenient manner. For this purpose, it is referred to in the claims as well as to the following explanations, that illustrate together with figures, how this invention is put in practice. In connection with these explanations, preferred arrangements and improved embodiments of the conclusions of the present invention are elucidated.

BRIEF DESCRIPTION OF THE DRAWING

FIG. 4 is a graph showing the activity of cathepsin B in various samples.

FIG. 5 is a graph showing the activity of cathepsin H in various samples.

FIG. 6 is a graph showing the activity of cathepsin L in various samples.

FIG. 7 is a graph showing the amount of protein of two samples per unit of time.

Figure 1:
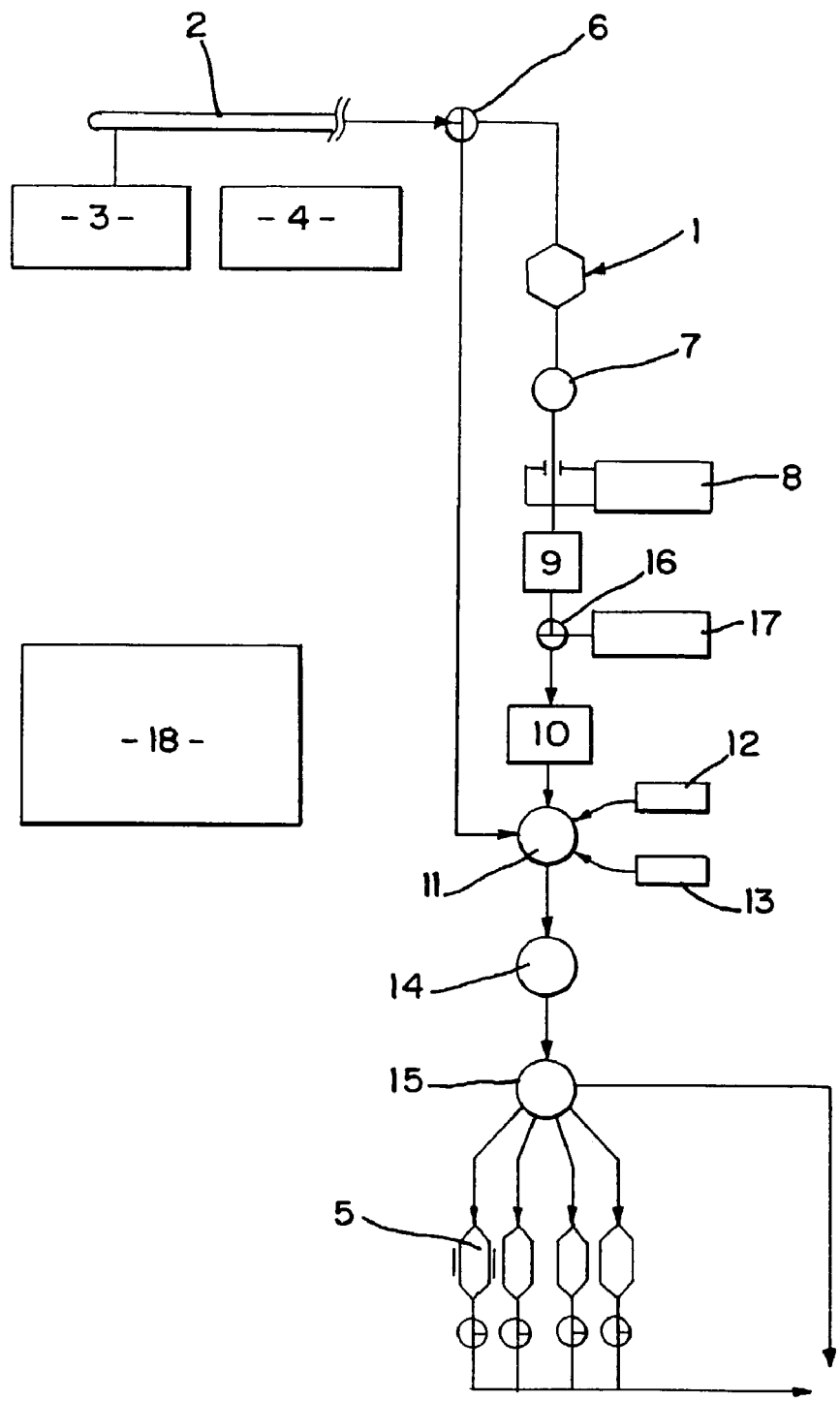
FIG. 1 illustrates schematically the sequence of the arrangement according to this invention.

This device as shown in FIG. 1 enables one to determine automatically and serially the enzyme activity of various fluid samples, such as homogenated tissues or all kinds of body fluids.

The device for analysing the sample comprises, according to the invention, a column 1 filled with a chromatographic carrier treated with a substance capable of binding such enzyme inhibitors, which correspond to at least one enzyme in the sample.

If one wishes to determine, for example, the activity of the enzyme cathepsin H in a sample, one may use Sepharose-gel as chromatographic carrier prepared with papain as to remove the enzyme inhibitors corresponding to cathepsin H.

A sample supply tube 2 is connected to the upper end of the column 1. 2 is in the illustrated device a portion for removing alternatively a sample from the sample supply 3 or column buffer from a reservoir 4.

A valve/pump arrangement is connected in series to the lower end of the column 1 to fill—according to the illustrated device—several test tubes 5 with a substrate and at least a portion of the sample.

A possible substrate for detecting the activity of cathepsin H in a sample is H-Arg-AMC. The cleavage products of this substrate H-Arg-AMC resulting from the reaction with the enzyme cathepsin H are H-Arg and AMC. As the enzyme activity is always proportional to the concentration of the cleavage products, it is possible to measure the enzyme activity by recording the concentration increase per unit of time of at least one of the cleavage products during the incubation. With cathepsin H as the enzyme the concentration increase of AMC is recorded. In the realized device as discussed above a fluorescence spectrometer is used as a detector but not characterized further in the only figure shown.

Subsequently, the various components of the device, according to the only illustrated figure, are explained in detail.

As already mentioned, the various samples are located in the sample supply 3 which may be a rondel, for example. By means of the portion 2 it is possible to withraw the samples from the sample supply automatically and to pass them through a valve 6 to the column 1. The chromatographic carrier of the column 1 is prepared in such a manner, that there is an excess of a substance, normally one or several enzymes, capable of binding the intended enzyme inhibitors in the sample. As a rule, there is a large excess of this substance in order to use the column repeatedly; that is, several samples can pass through the column. Moreover, the column 1 is exchangeable, so that, if the said substance is used up, the column 1 may replaced by a new one. The shape and dimensions of the column 1 depend on the intended capacity of the column 1 as well as on the portions joined to the column 1. For example, the column may have a large cross-section and a corresponding length or a small cross-section but a larger length.

To check the operating ability of the column 1, one has to measure regularly samples with known enzyme activity values. This is a simple way to check, whether the substance capable of binding enzyme inhibitors is used up.

To make sure, that a preceding sample will not mingle with the following different sample, one may feed the column by turns with the sample and with a column buffer from the reservoir via the portion 2 and the valve 6. This is done after each application of a sample by means of a pump 7, which is connected in series to the column 1.

A photometer as a control device 8 is connected in series to this pump 7 and therefore also in series to the column 1, in order to check the purity of the column buffer discharged from the column and the pump, respectively. Thus one makes sure, that, before the column 1 is fed with another sample, the liquid in the column is column buffer only.

After the sample had passed through the column, the column 1 is washed with column buffer as a wash liquid resulting in a diluted sample. A measuring device 9 is also connected in series to the column 1 and determines the degree of dilution by means of measuring the volume. As the original volume of the sample is known, the volume of the column buffer used for washing is detected only. The degree of dilution can now be calculated from the sum of the volumes of the sample and the column buffer.

A device 10 for mixing is connected in series to the measuring device 9 so as to homogenate the mixture of the sample and the column buffer.

The resulting homogenous mixture as well as the substrate from a substrate reservoir 12 and a measuring buffer from an appropriate reservoir 13 can be supplied to the test tubes 5 via a valve 11. The measuring buffer serves for establishing definite experimental conditions. Other solutions can be added alternatively or additionally to the mixture, for example a special inhibitor-solution serving as a titer for calibrating the concentration. For this the device has to be equipped with additional vessels for the corresponding solutions. Additionally, in the illustrated device a pump 14 and one more valve 15 is connected in series to valve 11 for passing on the now existing mixture of sample, column buffer, substrate and measuring buffer.

The entire device described in this paper can be thermostated. Normally, the enzyme inhibitors are removed from the sample at about 4° C. In particular, means, which are however not represented in the only figure, are provided to thermostate the test tubes 5. The test tubes should at least be thermostated during the incubation time. The standard temperature for this procedure is about 37° C. However, if there are special experimentell conditions, facilities may be convenient to select variable temperatures for thermostating. The incubation time, that is the time for reaction between sample and substrates, depends on the different enzymes and substrates, and as a rule, it is between 5 and 15 minutes.

It may be mentioned, that the inventive device enables one to carry out redundant measurements by measuring the activity of the same enzyme of a sample in different test tubes and also, after an appropriate preparation of the column, to measure the acivities of different enzymes of the same sample by using different substrates, that is, the treated sample reacts with different samples. Finally, it is possible, to determine the activity of one enzyme by reacting with different substrates.

The device as shown in FIG. 1 may be used in such a manner, that samples pass alternatively through the column or directly, via the valves 6 and 11, pump 14 and valve 15, into the test tubes. Therefore one may measure concurrently the enzyme activity of samples having passed through the column and samples having not passed through the column. Consequently, one is able to compare measurements of samples in the presence of enzyme inhibitors with measurements of samples, from which the enzyme inhibitors are removed; that is, to compare measurements carried out with untreated samples with measurements carried out with treated samples.

Additionally, there is also a valve 16 provided in the device shown in FIG. 1 in order to feed the entire apparatus with buffer 17 serving as a wash liquid.

By means of a computer 18 one may control the individual components of the inventive device, for example, the sample supply portion so as to feed the column with samples and column buffer. Moreover, the evaluation of the recorded measurements may be done by means of the computer 18.

To sum up, by means of the inventive process and device an efficient and largely automatical method for determining enzyme activities of fluid samples can be realized.

As a supplement, a process and a device is proposed for determining the activity of enzymes and/or the concentration of inhibitors both present in fluids.

This method may be used in additon or alternatively to the above explained method.

The determination of enzyme activities is very important for diagnosis in clinical chemistry and microbiology as well as in biochemical research. A lot of methods for such determinations are known and used as standard methods.

However, it has been impossible, to measure the activity of various enzymes in blood serum, other body fluids, or in cells, where they are produced, quickly and with a reasonable price, because many of them are partly or totally inhibited in order to protect their neighborhood; that is, where they could cause damage, they are mostly inactive.

If a pathological change arises in cells producing such enzymes, or in their neighborhood, the ratio of inhibited to active amount of enzyme may be changed in favor to the non inhibited, active form; especially in the blood serum, a resulting excess of enzyme is immediately reversibly blocked by inhibitors.

Therefore, the free activity of not inhibited enzymes in blood serum, for example, could only be measured by means of hitherto applied methods, if the concentration of the enzymes was extremly high.

However, it may be necessary for an early diagnosis of diseases, to measure reliably and as quickly as possible the increase of the total enzyme activity per unit of volume or the ratio of the activities per unit of volume of the inhibited to the free form, for the peak activities of the free portion of the enzyme as detectable by conventional methods often does not arises before an advanced status of the disease.

Moreover, to know the portion of the active form related to the total pool of the enzyme may also be important in research.

By means of immunoassays (ELISA) the concentration of even the inhibited portion of a class of enzymes can be determined. However, a considerable disadvantage of immunoassays is the impossibility to discriminate between the free and therefore active and the inhibited state of the enzyme, because these methods detect only the sum of both states of the enzyme together with enzymes, which have lost their catalytic function partly and totally. The measurement of activities by means of these methods is impossible.

Likewise, the known enzyme assays for measuring the enzyme activity can not discriminate between both states of the enzyme, as the free state can merely be measured by these methods.

How can the total activity of an enzyme present in both states, inhibited and free, be measured additionally to the activity of the free state?

The solution of this problem is simple and has a reasonable price.

By means of chromatography the specific inhibitors inhibiting the intended enzyme in its activity are removed from the sample, which may be human blood serum. Afterwards a conventional measurement of enzyme activity can be carried out.

By measuring the activity of the enzyme in the untreated sample, the portion of the free and the inhibited enzyme of the totally present amount of enzyme can be determined.

The following example may illustrate this process:

Papain, a cysteine protease, is bound to a Sepharose-gel, which serves as a carrier. The gel prepared in this way is filled in a column for chromatography. From a sample, such as homogenated tissue from a tumor of the lungs, incubated in-this column, all inhibitors are removed, that show a higher affinity to papain than to the enzymes, to which they are originally bound. Such enzymes may be among others cathepsin B, H and L. One of them, cathepsin H, normally is almost completely inhibited and its activity is only measurable after removing the inhibitors (stefin A, kininogen and others).

The measurement of the activities is carried out according to known assays by means of measuring fluorescence, using substrates and inhibitors suitable for the enzyme.

This process is feasible, according to the application, with the most different enzymes, inhibitors and materials for chromatography. It may be carried out completely automatically and therefore, it is qualified for routine measurements in the laboratory (for this see FIG. 1).

A large quantity of samples can so be stored in a sample supply, which may be a rondel or a suitable depot for samples. Thereof a definite volume of the sample can be directed occasionally in a suitable chromatographic column (1) via a device for discharging (2) by means of a pump connected in series to this portion (2).

After a fixed incubation time, this sample, from which the inhibitors are now removed, is discharged completely from the column and simultaneously diluted by passing a definite buffer solution through the column from a reservoir (4) of this buffer via the same way as described above for the sample.

A following measurement of the purity (8), by means of photometry or measurement of the electrical conductance, for example, enables one to prevent, that some of the sample remains on the column and that consumption of buffer is limited to the necessary amount.

By means of an additional device (9) the total volume discharged from the column can be measured.

A device (10) is connected in series to the column, to obtain a homogenous mixture of the sample and the buffer after being discharged from the column.

By means of an additional pump and via a valve, measuring buffer, substrate, the sample, which is diluted in a definite ratio with the initially used buffer solution, and, if need be, inhibitors, can be directed in a definite sequence to a device (5) for measuring the fluorescence. The said valve and all other functional units of the apparatus can be controlled by a computer (18).

The activity per unit of volume of the intended enzyme in the original sample as well as the activity per unit of mass, if the protein concentration is known, can now be calculated in a simple way by means of the computer.

To compare the enzyme activity, determined in the said manner, with the enzyme activity in the untreated sample, one can direct the sample through the apparatus without passing through the column.

After or even during the measuring process one can start a computer controlled flushing of the device with a wash liquid, in order to remove completely any residue of the sample.

There are additional explanations of FIG. 1 in the parent application.

To solve special problems in the best way by means of the described device, the arrangement of some units, in particular the valves, can differ from the arrangement shown in FIG. 1.

To improve the efficiency of the said device, it is convenient having several columns connected in series or parallel. this. Due to provided facilities for measuring the activity of different enzymes of the same sample in a parallel manner by means of fluorescence measurements; the efficiency of this device is also improved.

Instead of measuring the activity of specific enzymes by means of fluorescence measurements, one may carry out this determination by means of other methods such as photometry, according to need and the applied assay.

As a special item, one may take columns, repeatedly useable, and prepared with different substances such as different enzymes or enzyme fragments produced in a large technical scale, and one may also take chromatographic carriers linked with inhibitors.

Due to these numerous facilities, enzymes as well as inhibitors can be purified according to the applied column.

If a column prepared with enzymes is used up, the inhibitors removed from the samples can be separated from the enzymes by means of a simple chemical procedure and can be put to further use. In this way hitherto unknown inhibitors may be concentrated and characterized.

If a column prepared with inhibitors is applied, enzymes may be removed selectively from the sample and may be characterized. In an onologous manner, as described in the foregoing example, inhibitors, for example kinogen, are now removed instead of enzymes (such as cathepsin H). These inhibitors are analysed by means of specific assays in order to determine the concentration and activity of them in the original sample.

The figures explain the improved embodiment.

The efficiency of the above described column (the enzyme papain is coupled to Sepharose-gel, the gel serves as a chromatographic carrier) is demonstrated as an example by means of the following measurements carried out in connection with research on the proteinases cathepsin B, H and L:

1. In homogenated lung tissues of patients with tumors the activities (µU/mg protein) of cathepsin B, H and L are measured. This is done before and after removing the corresponding inhibitors by means of Sepharose-gel prepared with papain. The samples are incubated in the column for fixed 15 min.

Figure 2:
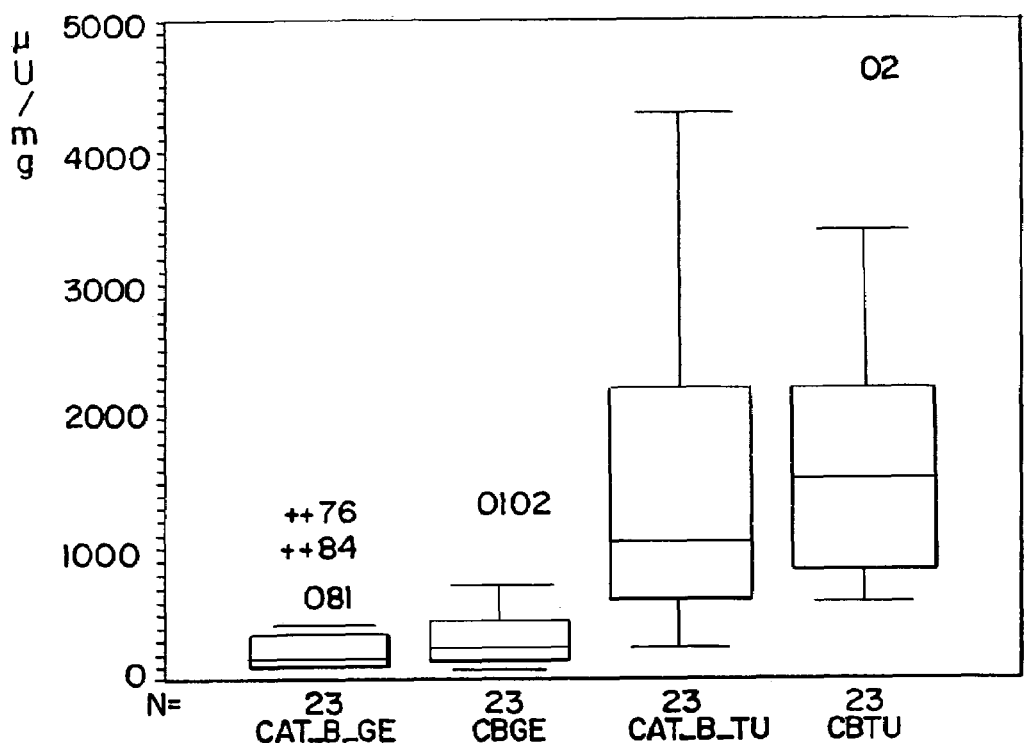
FIG. 2 is a graph showing the activity of cathepsin B in various samples.

FIG. 2 demonstrates, that the enzyme acitivity of tissue from lungs with a tumor as well as without a tumor is, according to the median values, substantially higher after removing the inhibitors by means of a column than in untreated samples.

In this graph, for every comparison of samples before and after removing the inhibitors, the same collective of samples is used. The increase of activities can only be interpreted through removing the inhibitors and goes along with the standard literature.

Figure 3:
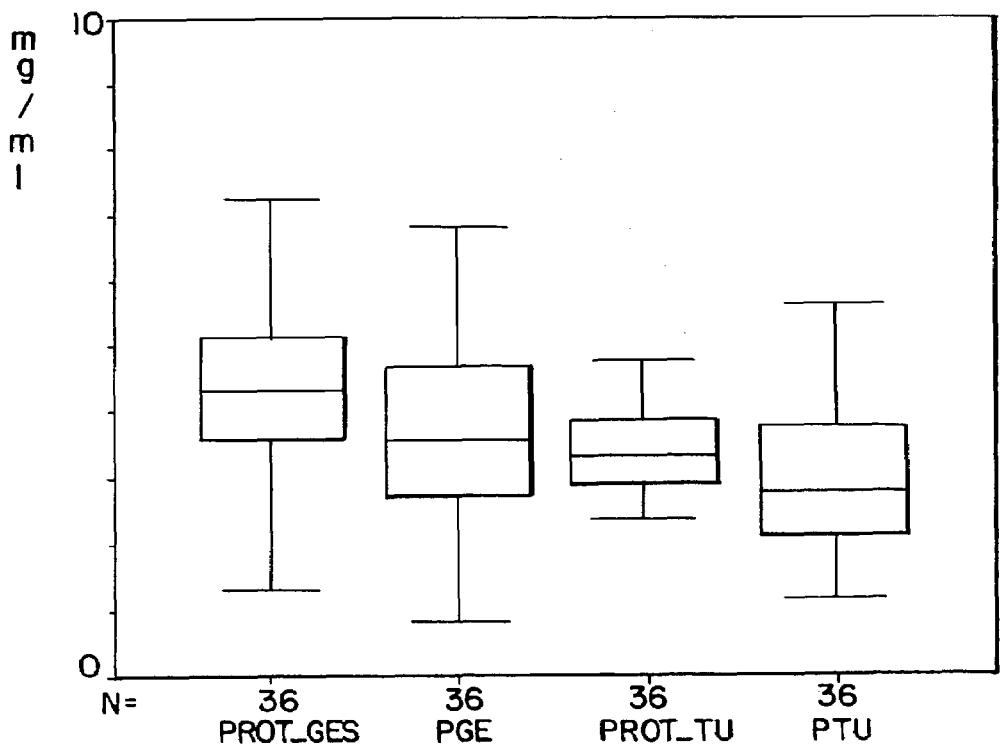
FIG. 3 is a graph showing the amount of protein in various samples.

2. FIG. 3 illustrates, that the amount of protein (mg/ml) according to the mean values is substantially higher before the withdrawing of the inhibitors by the papain column than afterwards. This can only be interpreted through the fact, that inhibitors are really removed.

3. As an example for demonstrating the time of withdrawing of inhibitor by papain, which is coupled to the column, a pair of samples was chosen by chance. The activities were determined after different times of incubation of the samples on the column.

FIG. 4 illustrates a rapid activity increase of cathepsin B, just beginning at the starting point and reaching a plateau after 15 minutes. The starting point (t=0 min) corresponds to the activity value before the removal of inhibitors.

FIGS. 5 and 6 illustrate also a large activity increase after short incubation times. The remaining activity resulting from the activity measurement of cathepsin L, as indicated in FIG. 6, is the activity of an enzyme not yet characterized.

4. FIG. 7 demonstrates the course af decrease of the amount of protein related to the sample described in the foregoing paragraph 3. Already after a short time the amount of protein reaches a minimum and proceeds in the following time to a plateau; this means, that, due to the excess of papain in the column, the inhibitors will be quickly and reliably bound.

Figure 8:
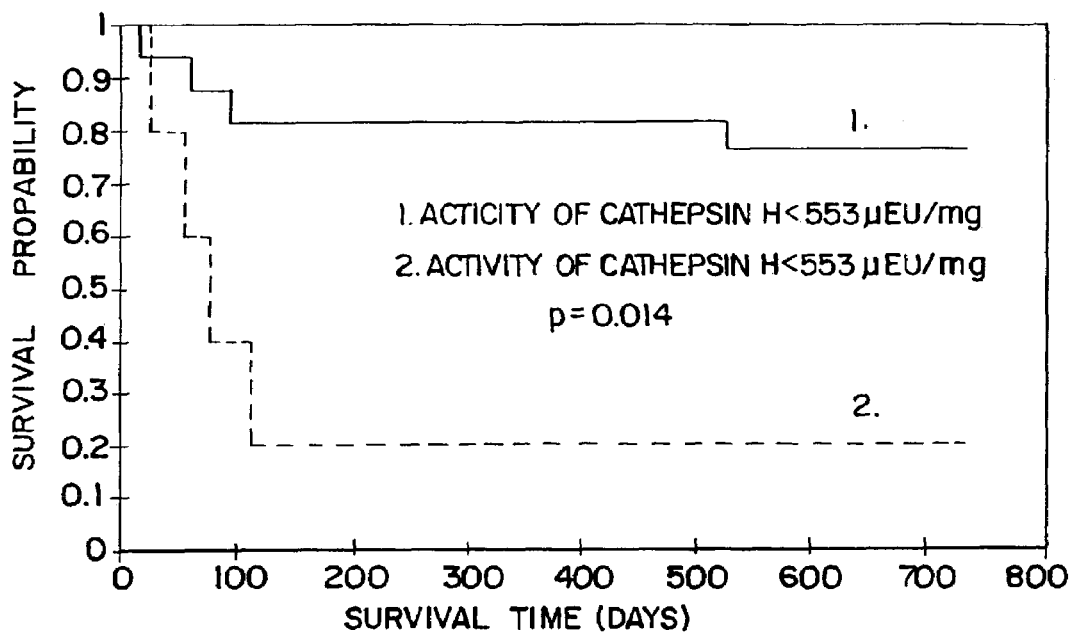
FIG. 8 is a survival graph showing the activity of cathepsin H of two samples.

5. The survival-graph (Kaplan-Meier-graph) in FIG. 8 demonstrates the following fact: the prognosis for survival-time of patients with a cathepsin H activity in the tissue of the tumor, that is beyond a threshold of 533 µEU/mg, is by far more unfavourable than with an activity below this threshold. The values in this and in all other above described figures originated from measurements carried out with a papain-column.

The following conclusions, for example, are to be drawn from the above described explanations:

In many body fluids, such as blood serum, urine or liquor as well as in homogenated tissues, suspensions of bacteria and other fluids, there are enzymes, which are inactivated by specific inhibitors. Up to now it was only possible in case of peak values, to determine the activity of these enzymes.

By means of immunoassays, such as the comparatively expensive ELISA assay, only the total amount of enzyme concentration can be measured, but not the activity of intact and therefore catalytically active forms of the enzyme.

It is now possible, by means of an appropriately prepared chromatographic column, to remove specific inhibitors from the sample in order to measure fractions and the total amount of the activity of one or several enzymes.

A side effect of this method is the purification and a concentration of specific inhibitors on the column. In a following step they can be separated from the chromatographic material in order to characterize them.

It is also possible, to bind inhibitors, producable in a large technical scale, instead of enzymes or enzyme fragments, which may also be produced in a large technical scale, to the chromatographic material, so as to characterize unknown enzymes as well as to determine the concentration and activity of the inhibitors present in this sample.

Due to the automation, the above described device or a required modification of it, can be used for routine measurements in clinical-chemical laboratories as well as in microbiological diagnosis and in biochemical research.

The chromatographic columns can be used several times and are of low production costs, therefore, it is possible to analyse in a short time a large number of samples with a reasonable price.

By establishing such a device, a field of research is disclosed, hitherto not treated due to a lack of appropriate techniques.

Due to the described process and device, it is possible, to make a prognosis of the course of a disease and of the survival time of the patient, in order to set a therapy adapted to the special requirements of the patient. It will be the task of research, to evaluate by means of the said process and device new and reliable tumor markers and parameters for checking the course of a disease.

The said process and device may also be significant for bacteriology and microbiology, because the biochemical classification of bacteria, for example, is of considerable significance for diagnosis.

The above described device is transportable only to a certain extend and not well adapted to carry out a quick test outside of a laboratory with a reasonable price. Therfore, a device, as described in the following section and based on the device illustrated in FIG. 1, is convenient for such a quick test.

Figure 9:
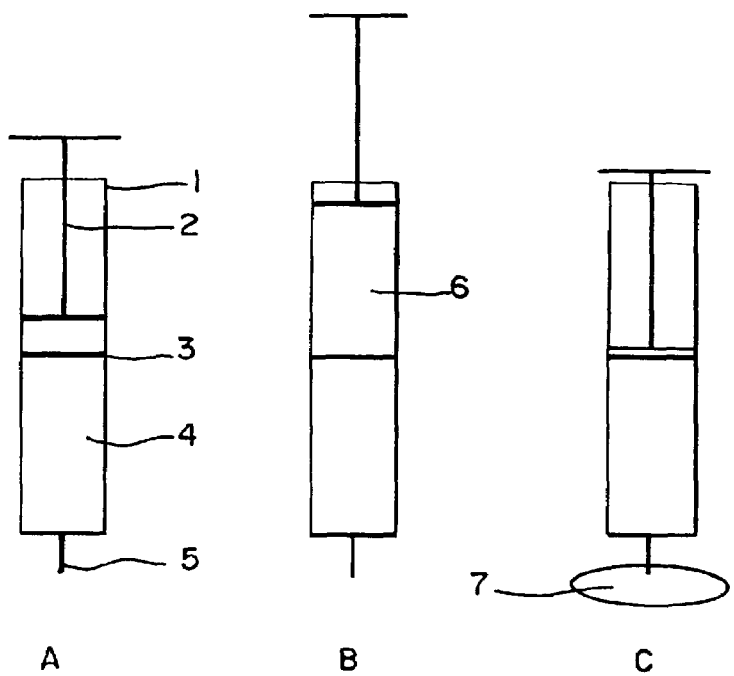
FIG. 9 is representation of device for a quick test.

FIG. 9 illustrates the improved embodiment.

A special syringe (1) represented schematically in states A, B and C, contains in the lower part, between two microfiltres (3 and a portion of 5), a chromatographic material, to which there are coupled, according to the above described process, enzymes, inhibitors or fragments thereof, which are produced in a large technical scala.

In the state before use, (A), there is a liquid, appropriate to the requirements, for example a wash liquid, above the chromatographic material and below the plunger (2) in a space (6) filled with liquid, To reach the state for reaction, (B), a sample, such as blood, blood serum, urine, liquor or another fluid, is sucked through the aperture (5) of the syringe, which is equipped with a microfilter, in the space, which contains the chromatographic material, by means of a vacuum, produced by the plunger (2). Subsequently, when the occasion arises, there is a definite incubation time. In the state for reaction, according to the chromatographic material, enzymes or, in the case of papain bound to Sepharose-gel, inhibitors such as kininogens, are removed from the sample.

After that, the so treated sample together with the liquid, which is in state A above the filter and below the plunger (2), is discharged in a rection vessel (7) by means of a pressure produced by the plunger (C).

The reaction vessel may contain a specific substrate, which is, for example, specifically cleaved by enzymes, in order to get a color change, like an indicator. These enzymes have just been released from their inhibitors by the foregoing procedure.

After a definite time, the result of this quick test can be recorded, by means of the color change in the reaction vessel, for example.

Due to this process, it is possible without a bulky laboratory apparatus, that is based on the device illustrated in FIG. 1, to do useful diagnosing and prognosing, although the efficiency and precision of a laboratory apparatus is not achieved. Such a quick test may be carried out to do diagnosing in clinical and preclinical emergency cases as well as in general practise.

The invention claimed is:

1. A device for measuring the activity of an enzyme in a liquid sample that includes at least one enzyme and at least one enzyme inhibitor corresponding to the enzyme, the device comprising:
   a flow through column;
   a means for measuring the activity of said enzyme; and
   at least one valve assembly capable of supplying a portion of the liquid sample through the column or outside of the column, and to the means for measuring the activity of said enzyme;
   the column including a chromatographic carrier having a substance capable of binding said enzyme inhibitor corresponding to said enzyme in a sample, the substance bound to the carrier effective for binding said enzyme inhibitor with a higher binding affinity than said enzyme, the column being capable of delivering at least a part of the sample discharged from the column to the means for measuring the activity of said enzyme.

2. The device according to claim 1 wherein the chromatographic carrier contains an excess amount of substance capable of binding said enzyme inhibitor relative to the amount of inhibitor in a sample such that the column containing the chromatographic carrier can be used repeatedly.

3. The device according to claim 1 wherein the column is exchangeable.

4. The device according to claim 1 wherein the means for measuring activity is a fluorescence detector.

5. The device according to claim 1 wherein the device further comprises a valve/pump assembly between the column and the means for measuring activity of said enzyme.

6. The device according to claim 5 wherein the valve/pump assembly is capable of delivering a measuring buffer to the sample after it has left the column.

7. The device according to claim 1 wherein the device further comprises a control device for determining purity of a buffer discharged from the column.

8. The device according to claim 7 wherein the control device functions photometrically.

9. The device according to claim 1 further comprising a measuring device for determining dilution of a sample discharged from the column.

10. The device according to claim 1 wherein the means for measuring the activity of said enzyme and column are independently thermostated.

11. The device according to claim 1 further comprising at least one valve assembly capable of supplying a wash buffer to the column.

12. The device according to claim 1 further comprising an electronic control means for elution of sample out of the column.

13. The device according to claim 1 wherein the substance bound to the carrier effective for binding an enzyme inhibitor is papain.

14. A device for measuring the activity of an enzymes in a liquid sample that includes at least one enzyme and at least one enzyme inhibitor corresponding to said enzyme, the device comprising:
   a flow through column filled with a solid carrier and a substance bound to the carrier, the substance bound to the carrier effective for binding said enzyme inhibitor with a higher binding affinity than said enzyme;
   a means for measuring activity of the said enzyme, the flow through column effective for delivering a part of a sample discharged from the column to a means for measuring the activity of said enzyme;
   at least one valve assembly capable of supplying a portion of the liquid sample through the column or outside of the column, and to the means for measuring the activity of said enzyme; and
   a control means effective for checking purity of liquid sample discharged from the column, wherein the control means includes a photometer or a means for measuring conductivity;
   wherein the flow through column and means for measuring the activity of said enzyme are independently thermostated.

15. The device according to claim 14 wherein the substance bound to the carrier effective for binding an enzyme inhibitor is papain.

16. A device for measuring the activity of an enzymes in a liquid sample that includes at least one enzyme and at least one enzyme inhibitor corresponding to said enzyme, the device comprising:
   a flow through column filled with a solid carrier and a substance bound to the carrier, the substance bound to the carrier effective for binding said enzyme inhibitor with a higher binding affinity than said enzyme;

a means for measuring the activity of said enzyme, the flow through column effective for delivering a part of a sample discharged from the column to a means for measuring the activity of said enzyme;

at least one valve assembly capable of supplying a portion of the liquid sample through the column or outside of the column, and to the means for measuring the activity of said enzyme; and a measuring means effective for determining dilution of sample discharged from the column;

wherein the flow through column and means for measuring the activity of said enzyme are independently thermostated, wherein the device includes a computer effective for automatic control and operation of feeding of test samples onto the flow through column, determination of buffer dilution, mixing of sample from the flow through column in the detection means, and recording and evaluation of results.

17. The device according to claim 16 wherein the substance bound to the carrier effective for binding an enzyme inhibitor is papain.

18. A device for measuring the activity of an enzyme in a liquid sample that includes at least one enzyme and at least one enzyme inhibitor corresponding to said enzyme, the device comprising:

a flow through column; and a means for measuring the activity of said enzyme, the column including a chromatographic carrier having a substance capable of binding said enzyme inhibitors corresponding to said enzyme in a sample, the substance bound to the carrier effective for binding said enzyme inhibitor with a higher binding affinity than said enzyme, the column being capable of delivering at least a part of the sample discharged from the column to the means for measuring the activity of said enzyme, wherein the means for measuring the activity of said enzyme and said column are independently thermostated.

19. A device for measuring the activity of enzymes in a liquid sample that includes at least one enzyme and at least one enzyme inhibitor corresponding to said enzyme the device comprising:

a means for measuring said activity;

a flow through column;

a sample supply and column buffer reservoir effective for providing sample and buffer to the flow through column;

at least one test vessel for collection of a sample from the flow through column; and a subsftate reservoir effective for supplying substrate to the test vessel, the column including a chromatographic carrier having a substance capable of binding said enzyme inhibitors corresponding to said enzyme in said sample, the substance bound to the carrier effective for binding said enzyme inhibitor with a higher binding affinity than said enzyme, wherein said test vessel is a part of said measuring means for measuring said activity and is independently thermostated from said column.

* * * * *